(12) United States Patent
Pantell et al.

(10) Patent No.: US 9,636,524 B2
(45) Date of Patent: May 2, 2017

(54) NEUTRON SOURCE FOR NEUTRON CAPTURE THERAPY

(71) Applicant: Adelphi Technology, Inc., Redwood City, CA (US)

(72) Inventors: Richard Harris Pantell, Portola Valley, CA (US); Charles Kevin Gary, Palo Alto, CA (US); Melvin Arthur Piestrup, Woodside, CA (US)

(73) Assignee: Adelphi Technology, Inc., Redwood City, CA (US)

( * ) Notice: Subject to any disclaimer, the term of this patent is extended or adjusted under 35 U.S.C. 154(b) by 0 days.

(21) Appl. No.: 14/190,389

(22) Filed: Feb. 26, 2014

(65) Prior Publication Data

US 2014/0179978 A1    Jun. 26, 2014

Related U.S. Application Data

(62) Division of application No. 13/532,447, filed on Jun. 25, 2012, now abandoned.

(60) Provisional application No. 61/571,406, filed on Jun. 27, 2011.

(51) Int. Cl.
*A61N 5/10* (2006.01)
*G21K 5/08* (2006.01)

(52) U.S. Cl.
CPC ............ *A61N 5/1077* (2013.01); *A61N 5/10* (2013.01); *A61N 2005/109* (2013.01); *A61N 2005/1094* (2013.01)

(58) Field of Classification Search
CPC .............................................. A61N 2005/109
See application file for complete search history.

(56) References Cited

U.S. PATENT DOCUMENTS

| | | | | |
|---|---|---|---|---|
| 4,112,306 A | * | 9/1978 | Nunan | A61N 5/10 315/502 |
| 5,392,319 A | * | 2/1995 | Eggers | H05H 6/00 376/151 |
| 5,703,918 A | * | 12/1997 | Hiismaki | A61N 5/10 376/458 |
| 5,903,622 A | * | 5/1999 | Yoon | H05H 3/06 376/110 |
| 6,925,137 B1 | * | 8/2005 | Forman | H05H 3/06 376/108 |

(Continued)

OTHER PUBLICATIONS

Cerullo et al., "An irradiation facility for Boron Neutron Capture Therapy application based on a radio frequency driven D-T neutron source and a new beam shaping assembly," Rev. Sci. Inst. v. 73, No. 10 (2002).*

(Continued)

*Primary Examiner* — Sean P Burke
(74) *Attorney, Agent, or Firm* — Donald R. Boys; Central Coast Patent Agency, Inc.

(57) ABSTRACT

A therapy apparatus for producing thermal neutrons at a tumor site in a patient has a plurality of fast neutron sources surrounding a moderator, a fast neutron reflecting media around the fast neutron sources, a gamma-ray and neutron shielding media surrounding the fast neutron reflecting media, and a patient chamber positioned inside the moderator. The fast neutron sources are positioned around the moderator to maximize and direct the neutron flux to said tumor site.

8 Claims, 12 Drawing Sheets

(56) References Cited

U.S. PATENT DOCUMENTS

| | | | | |
|---|---|---|---|---|
| 2009/0110146 A1* | 4/2009 | Sliski | ............... | A61N 5/10 378/65 |
| 2010/0061500 A1* | 3/2010 | Lou | ............... | G21G 4/02 376/114 |
| 2010/0176309 A1* | 7/2010 | Mackie | ............... | A61N 5/10 250/492.3 |
| 2012/0228522 A1* | 9/2012 | Sasai | ............... | A61N 5/1081 250/492.3 |

OTHER PUBLICATIONS

Verbeke et al., "Neutron Beam Optimization for Boron Neutron Capture Therapy Using the D-D and D-T High-Energy Neutron Sources," Nucl. Tech. p. 257-278 Feb. 2000.*

Koivunoro et al., "BNCT dose distribution in liver with epithermal D-D and D-T fusion-based neutron beams," Appl. Rad. and Isotopes 61 (2004) p. 853-859 (2004).*

Barth et al., "Boron Neutron Capture Therapy of Cancer: Current Status and Future Prospects," Clin. Cancer Res., 11:3987-4002 (2005).*

Pinelli et al., "TAOrMINA: From the First Idea to the Application to the Human Liver," Research and Development in Neutron Capture Therapy 1065-1072 (2002).*

Barth et al., "Boron neutron capture therapy for the treatment of glioblastomas and extracranial tumours: As effective, more effective or Less effective than photon irradiation?" Radiotherapy and Oncology 82 (2007) 119-122.*

Kawabata et al., "Survival benefit from boron neutron capture therapy for the newly diagnosed glioblastoma patients," Appl. Rad. and Isotopes 67 (2009) S15-S18.*

Suziki et al., "Dosimetric Study of Boron Neutron Capture Therapy With Borocaptate Sodium (BSH)/Lipiodol Emulsion (BSH/Lipiodolbnct) for Treatment of Multiple Liver Tumors," Int. J. Radiation Oncology Biol. Phys. vol. 58, No. 3 pp. 8920896 (2004).*

Kankaanranta et al., "Boron Neutron Capture Therapy in the Treatment of Locally Recurred Head and Neck Cancer" Int. J. Rad. Oncology Biol. Phys. (preprint) (2007).*

Vitale et al., "Malignant Tumors of the Liver," (Abstract) Aug. 1986.*

* cited by examiner

NEUTRON SOURCE FOR NEUTRON CAPTURE THERAPY

CROSS REFERENCED TO RELATED APPLICATIONS

This application is a divisional application of co-pending Ser. No. 13/532,447, filed Jun. 25, 2012 and titled "Neutron Source for Neutron Capture Therapy", which is a non-provisional application of provisional patent application Ser. No. 61/571,406, filed Jun. 27, 2011, by the present inventors. Disclosures of the prior applications are incorporated herein in their entirety by reference.

BACKGROUND OF THE INVENTION

1. Field of the Invention

This invention is in the technical area of apparatus and methods for generating neutrons for cancer therapy.

2. Description of Related Art

Thermal neutrons have been used for cancer therapy for the destruction of cancer tumors. These neutrons interact with boron-10 that has been placed at the cancer site. The neutrons interact with the boron to produce fission events whereby alpha particles and lithium nuclei are created. These massive ionized particles are then released, destroying the chemical bonds of nearby cancer tumor cells. At present the neutrons created in a reactor or accelerator pass through a moderator, which shapes the neutron energy spectrum suitable for Boron Neutron Capture Therapy (BNCT) treatment. While passing through the moderator and then the tissue of the patient, the neutrons are slowed by collisions and become low energy thermal neutrons. The thermal neutrons undergo reactions with the boron-10 nuclei, forming compound nuclei (excited boron-11), which then promptly disintegrate to lithium-7 and an alpha particle. Both the alpha particle and the lithium ion produce closely spaced ionizations in the immediate vicinity of the reaction, with a range of approximately 5-9 micrometers, or roughly the thickness of one cell diameter. The release of this energy destroys surrounding cancer cells. This technique is advantageous since the radiation damage occurs over a short range and thus normal tissues can be spared.

Gadolinium can also be considered as capture agent in neutron capture therapy (NCT) because of its very high neutron capture cross section. A number of gadolinium compounds have been used routinely as contrast agents for imaging brain tumors. The tumors have absorbed a large fraction of the gadolinium, making gadolinium an excellent capture agent for NCT.

The following definitions of neutron energy ranges, E, are used frequently by those skilled in the art of producing and using neutrons for medical, commercial and scientific applications: Fast (E>1 MeV), Epithermal (0.5 eV<E<1 Mev) and Thermal (E<0.5 eV) neutrons.

BNCT has the potential to treat previously untreatable cancers such as glioblastoma multiforme (GBM). In the US brain tumors are the second most frequent cause of cancer-related deaths for males under 29 and females under 20. GBM is nearly always fatal and has no known effective treatment. There are approximately 13,000 deaths per year due to primary brain tumors.

If conventional medicine is used where the glioblast is excised, new tumors almost invariably recur, frequently far from the original tumor site. Effective radiation therapy, therefore, must encompass a large volume and the radiation must be uniformly distributed. Conventional radiation treatment is usually too toxic to be of use against GBM.

For distributed tumors, effective radiation therapy must encompass a larger volume and the radiation must be uniformly distributed. This is also true of liver cancers. The liver is the most common target of metastases from many primary tumors. Primary and metastatic liver cancers are usually fatal, especially after resection of multiple individual tumors. The response rate for nonresectable hepatocellular carcinoma to traditional radiation treatment or chemotherapy is also very poor. However, recent results indicate that the thermal neutron irradiation of the whole liver with a $^{10}B$ compound could be a way to destroy all the liver metastases.

Recent research in BNCT has shown that neutron capture therapy can be used to treat a large number of different cancers. BNCT has been found to be effective and safe in the treatment of inoperable, locally advanced head and neck carcinomas that recur at sites that were previously irradiated with traditional gamma radiation. Thus BNCT could be considered for a wider range of cancers. BNCT holds such promise because the dose to the cancer site can be greatly enhanced over that produced by γ-radiation sources. This is a consequence of the fact that the neutron-boron reaction produces the emission of short-range (5-9 um distance) radiation, and consequently normal tissues can be spared. In addition boron can achieve a high tumor-to-brain concentration ratio, as much as ten or more, thereby preferentially destroying abnormal tissue.

BNCT has been tested using either nuclear reactors or accelerators, which are not practical or affordable for most clinical settings. Reactors also do not produce an ideal neutron spectrum and are contaminated with γ-radiation.

Fusion generators produce fast neutrons from the deuterium-deuterium (DD) or the deuterium-tritium (DT) reactions and are, in general, smaller and less expensive than accelerators and reactors. These fast neutrons must be moderated or slowed down to thermal or epithermal neutron energies using, for example, water or other hydrogen bearing materials.

The fusion neutron generator has three basic components: the ion source, the electron shield and the acceleration structure with a target. The ions are accelerated from the ion source to a titanium target using a high voltage potential of between 40 kV to 200 kV, which can be easily delivered by a modern high voltage power supply. An electron shield is usually disposed between the ion source and the titanium target. This shield is voltage biased to repel electrons being generated when the positive D+ ions strike the titanium target. This prevents these electrons from striking the ion source and damaging it due to electron heating.

The target uses a deuterium $D^+$ or tritium $T^+$ absorbing material such as titanium, which readily absorbs the $D^+$ or $T^+$ ions, forming a titanium hydride. Succeeding $D^+$ or $T^+$ ions strike these embedded ions and fuse, resulting in DD, DT or TT reactions and releasing fast neutrons.

Prior attempts at proposing fusion generators required the use of the DT reaction with the need for radioactive tritium and high acceleration powers. High yields of fast neutrons/sec were needed to achieve enough thermal neutrons for therapy in a reasonable length of time of therapy treatments. These prior schemes for achieving epithermal neutron fluxes are serial or planar in design: a single fast neutron generator is followed by a moderator, which is followed by the patient. Unfortunately, since the neutrons are entering from one side of the head, the planar neutron irradiation system leads to a high surface or skin dosage and a decreasing neutron dose deeper into the brain. The brain is not irradiated uniformly and cancer sites have lower thermal neutron dosage the further they are from the planar port.

Figure 1:
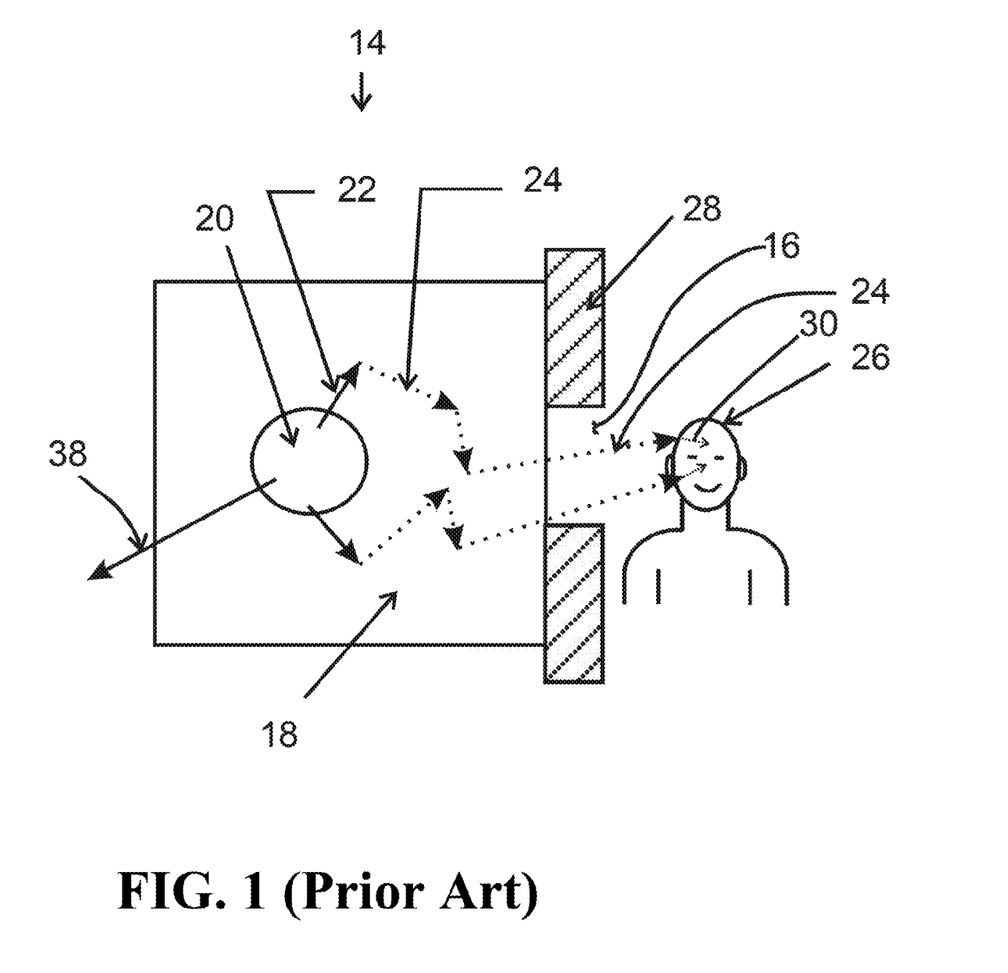
FIG. 1 (Prior Art) is a cross sectional view of a planar geometry for introducing thermal neutrons into a patient's brain.

A conventional planar neutron irradiation system 14 and its operation is shown in FIG. 1 labeled Prior Art. Conversion of fast neutrons 22 to thermal neutrons 30 takes place in a series of steps. First the fast neutrons 22 are produced by a cylindrical fast neutron generator 20 and then enter a moderating means 18 where they suffer elastic scatterings (collisions with nuclei of the moderating material's atoms). This lowers the fast neutrons to epithermal neutron 24 energies. A mixture of epithermal 24 and thermal neutrons 30 are emitted out of a planar port 16 and then enter the patient's head 26. The epithermal neutrons 24 are moderated still further in the patient's brain and moderated further to thermal neutrons, finally being captured by the boron at the tumor site. The fission reaction occurs and alpha and Li-7 ions are released, destroying the tumor cells.

The epithermal and thermal neutrons reach the patient's head through a planar port 16 formed from neutron absorbing materials that form a collimating means 28. The thermal and epithermal neutrons strike the patient's head on one side, and many neutrons escape or are not used. One escaping neutron 38 is shown. This is an inefficient process requiring a large amount of fast neutrons to be produced in order to produce enough thermal neutrons for reasonable therapy or treatment times (e.g. 30 min).

To achieve higher yields of fast neutrons the planar neutron irradiation system 14 requires that one use either the DD fusion reaction with extremely high acceleration powers (e.g. 0.5 to 1.5 Megawatts) or the DT reaction which has an approximate 100 fold increase in neutron yield for the same acceleration power.

The use of tritium has a whole host of safety and maintenance problems. Tritium gas is radioactive and extremely difficult to eliminate once it gets on to a surface. In the art of producing fast neutrons this requires that the generator be sealed and have a means for achieving a vacuum that is completely sealed. The generator head can not be easily maintained and usually its lifetime is limited to less than 2000 hours. This reduces the possible use of this generator for clinical operation since the number of patients who could be treated would be small before the generator head would need replacement.

On the other hand, the use of the DD fusion reaction allows one skilled in the art to use an actively-pumped-vacuum means with roughing and turbo pumps. The generator can then be opened for repairs and its lifetime extended. This makes the DD fusion reaction neutron generator optimum for clinical use. The downside for the DD fusion reaction is that high acceleration powers are required to achieve the desired neutron yield required by prior art methods. Improving the efficiency of producing the right thermal neutron flux at the cancer site is imperative for achieving BNCT in a clinical and hospital setting.

SUMMARY OF THE INVENTION

The invention in one embodiment is a neutron irradiation system that permits boron neutron capture therapy (BNCT) for cancer. It does this by delivering a uniform dose of thermal neutrons across the body organ (e.g. brain, liver or other organ) with a higher dose of neutrons to the tumor site over that of the healthy tissue and skin. This is accomplished with a unique neutron source that can be conveniently situated in a clinic, an outpatient facility, or a research laboratory. In one embodiment the neutron irradiation system uses the DD reaction at reasonable acceleration power levels and is relatively inexpensive and compact enough to be used in hospitals. The invention in one embodiment consists of multiple fast neutron sources (N≥2) arranged around a hemispherical or cylindrical moderator made of aluminum fluoride, heavy water or other efficient moderating materials. The fast-neutron source geometry is matched with the moderator and the patient's brain or body in a synergistic fashion to produce a uniform thermal neutron dose and therapeutic ratio across the brain or body part. In this embodiment the required fast neutron yield is almost two orders of magnitude smaller than that required from the prior art that uses a planar geometry. This permits using a safe DD reaction and lower electrical power and is critical for the development of a clinic-based system.

DETAILED DESCRIPTION

In the following descriptions reference is made to the accompanying drawings that form a part hereof, and in which are shown by way of illustration specific embodiments in which the invention may be practiced. It is to be understood that other embodiments may be utilized and structural changes may be made without departing from the scope of the present invention.

Uniform Delivery of Thermal Neutrons to the Brain

To achieve extremely high thermal neutron fluxes uniformly distributed across a patient's head, a hemispherical geometry is used in one embodiment of the invention. This unique geometry arranges fast neutron sources in a circle around a moderator whose radial thickness is optimized to deliver a maximum thermal neutron flux to a patient's brain. This embodiment produces a uniform thermal neutron dose within a factor of $1/20^{th}$ of the required fast neutron yield and line-voltage input power of a conventional planar neutron irradiation system. This permits using a relatively safe deuterium-deuterium (DD) fusion reaction (no radioactive tritium) and commercial high voltage power supplies operating at modest powers (50 to 100 kW).

Figure 2:
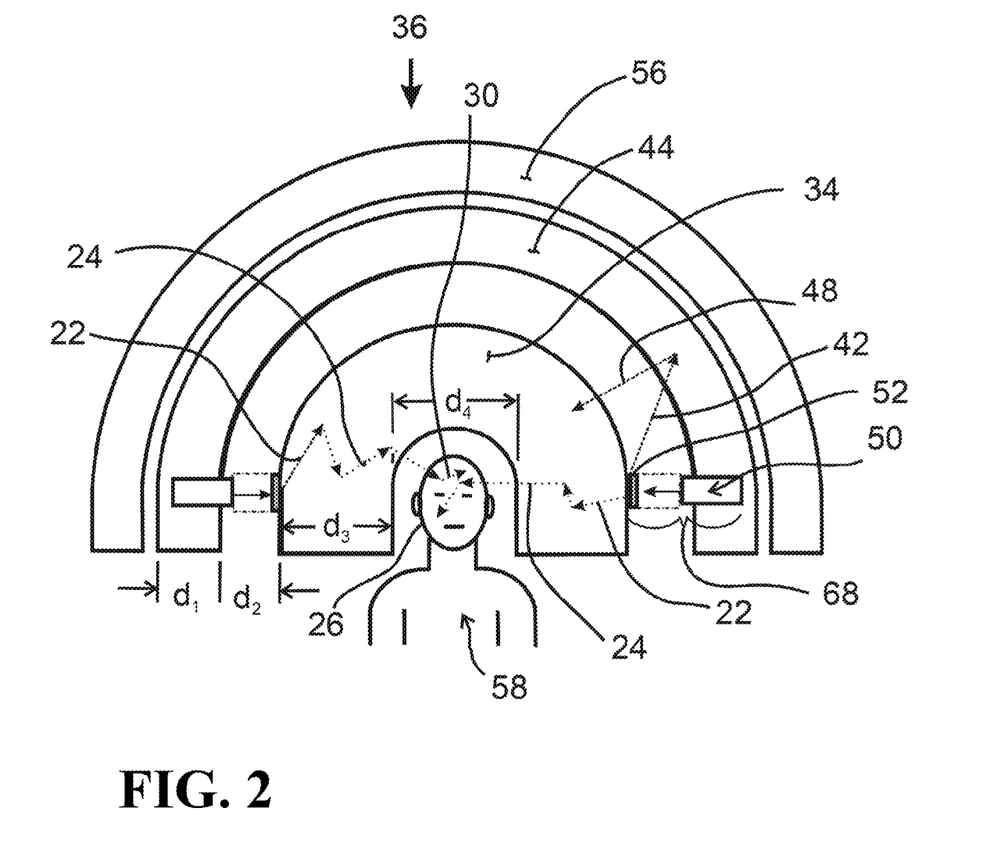
FIG. 2 is a cross sectional view of an embodiment of how multiple fast neutron generators are arranged around a hemispheric moderator to introduce a uniform thermal neutron dose into a patient's head.

FIG. 2 is a cross sectional view of a hemispheric neutron irradiation system 36 according to one embodiment of the invention. Multiple fast neutron generators 68 surround a hemispheric moderator 34, which in turn surrounds the patient's head 26. Titanium targets 52 are distributed around the perimeter of the hemispheric moderator 34. Surrounding the moderator 34 and the fast neutron generators 68 is a fast-neutron reflector 44.

In the moderator 34, moderating material such as $^7$LiF, high density polyethylene (HDPE), and heavy water are shaped in a hemisphere that is shaped around the head of the patient. The optimum thickness of the hemispheric moderator for irradiation purposes is dependent upon the material nuclear structure and density.

Figure 3:
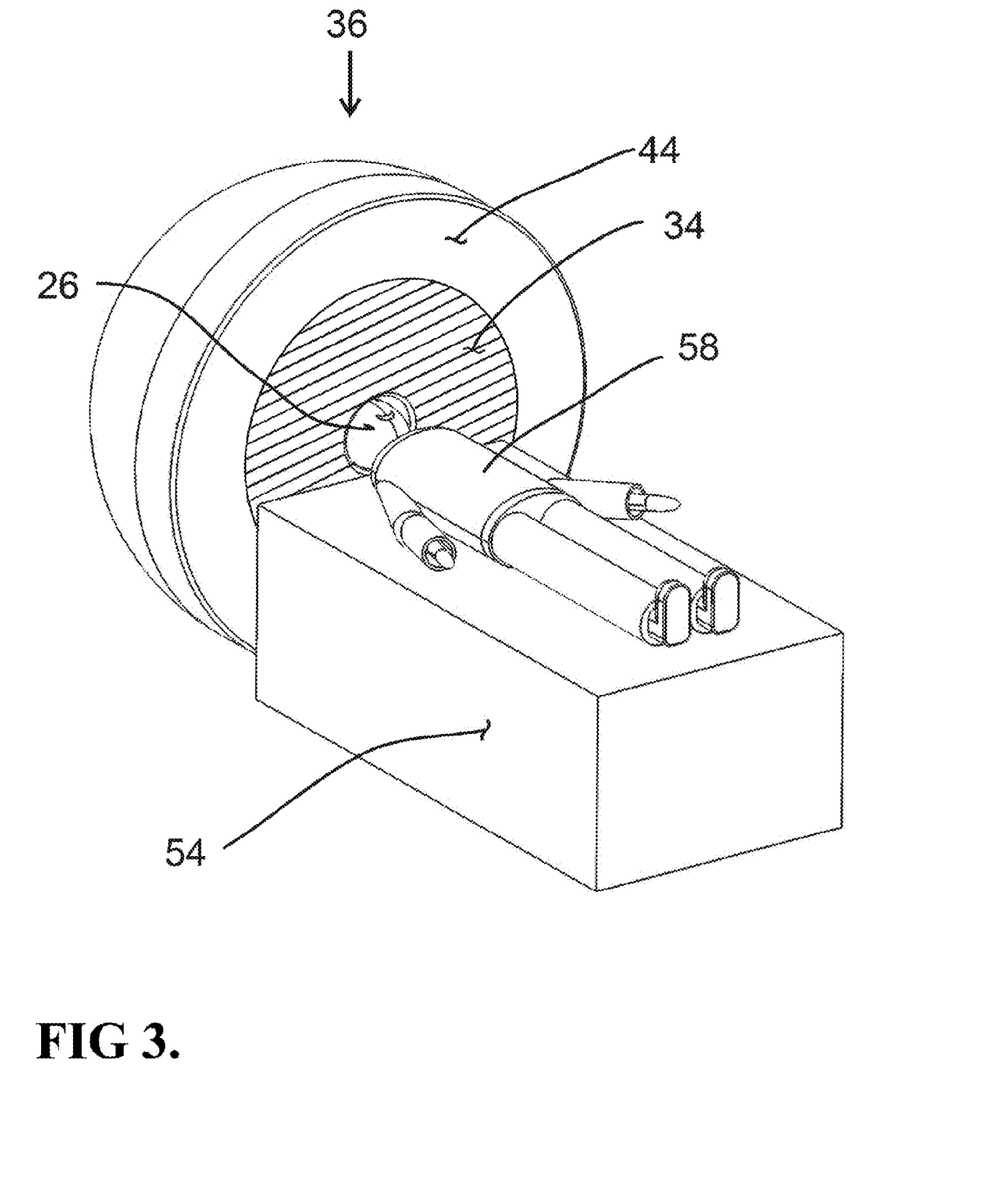
FIG. 3 is a perspective view of how multiple fast neutron generators are used in an embodiment of the invention to develop a high neutron dose into a patient's head.

FIG. 3 shows a perspective view of a patient 58 on a table 54 with the patient's head inserted into hemispheric irradiation system 36. The patient 58 lies on the table 54 with his head inserted into hemispheric moderator 34. Surrounding the moderator is neutron reflecting material, such as lead or bismuth.

Referring again to FIG. 2, fast neutrons 22 are produced by fast neutron generators 68. Generators 68 are composed of titanium targets 52 and ion sources 50. Ion beams are produced by ion sources 50 and accelerated toward titanium targets 52 which are embedded in hemispheric moderator 34. A DD fusion reaction occurs at the target, producing 2.5 MeV fast neutrons 22.

The fast neutrons 22 enter the moderator 34 wherein they are elastically scattered by collisions with the moderator atoms' nuclei. This slows them down after a few collisions to epithermal neutrons 24 energies. These epithermal neutrons 24 enter the patient's head 26 wherein they are moderated further to thermal neutron 30 energies. These thermal neutrons 30 are then captured by boron-10 nuclei at the cancer site, resulting in a fusion event and the death of the cancer cells.

Fast neutrons 22 are emitted isotropically from titanium target 52 in all directions. Outwardly traveling fast neutrons 42 are reflected back (reflected neutron 48) by fast neutron reflector 44, while inwardly traveling fast neutrons 40 are moderated to epithermal energies and enter the patient's head 26, where further moderation of the neutrons to thermal energies occurs.

A shell of protective shielding 56 is also shown in FIG. 2. In some embodiments this may be necessary for shielding both the patient and the operator from excessive irradiation due to neutrons, x-rays and gamma radiation. The shielding can be made of a variety of materials depending upon the radiation component one wishes to suppress.

In some embodiments fast neutron reflector 44 is made of lead or bismuth. The fast neutron reflector also acts as a shielding means to reduce emitted gamma rays and neutrons from the hemispherical neutron irradiation system 36. As one skilled in the art will realize, gamma absorbing or other neutron reflector means can be placed in layers around the hemispherical neutron irradiation system 36 to reduce spurious and dangerous radiation from reaching the patient 58 and the operator.

Hemispheric moderator 34, fast neutron reflector 44 and head 26 act together to concentrate the thermal neutrons in the patient's head. The patient's head and the moderator 34 act in concert as a single moderator. With a careful selection of moderating materials and geometry, a uniform dose of thermal neutrons can be achieved across the patient's head and, if a boron drug is administered, a large and uniform therapeutic ratio can be achieved.

The invention gives a uniform dose of thermal neutrons to the head while minimizing the fast neutron and gamma contributions. The required amount of fast neutrons to initiate this performance is reduced compared to that of prior art planar neutron irradiation systems (see FIG. 1).

FIG. 3 is a perspective view of the patient 58 on a table 54 with his head 26 in the hemispherical neutron irradiation system 36.

Figure 4:
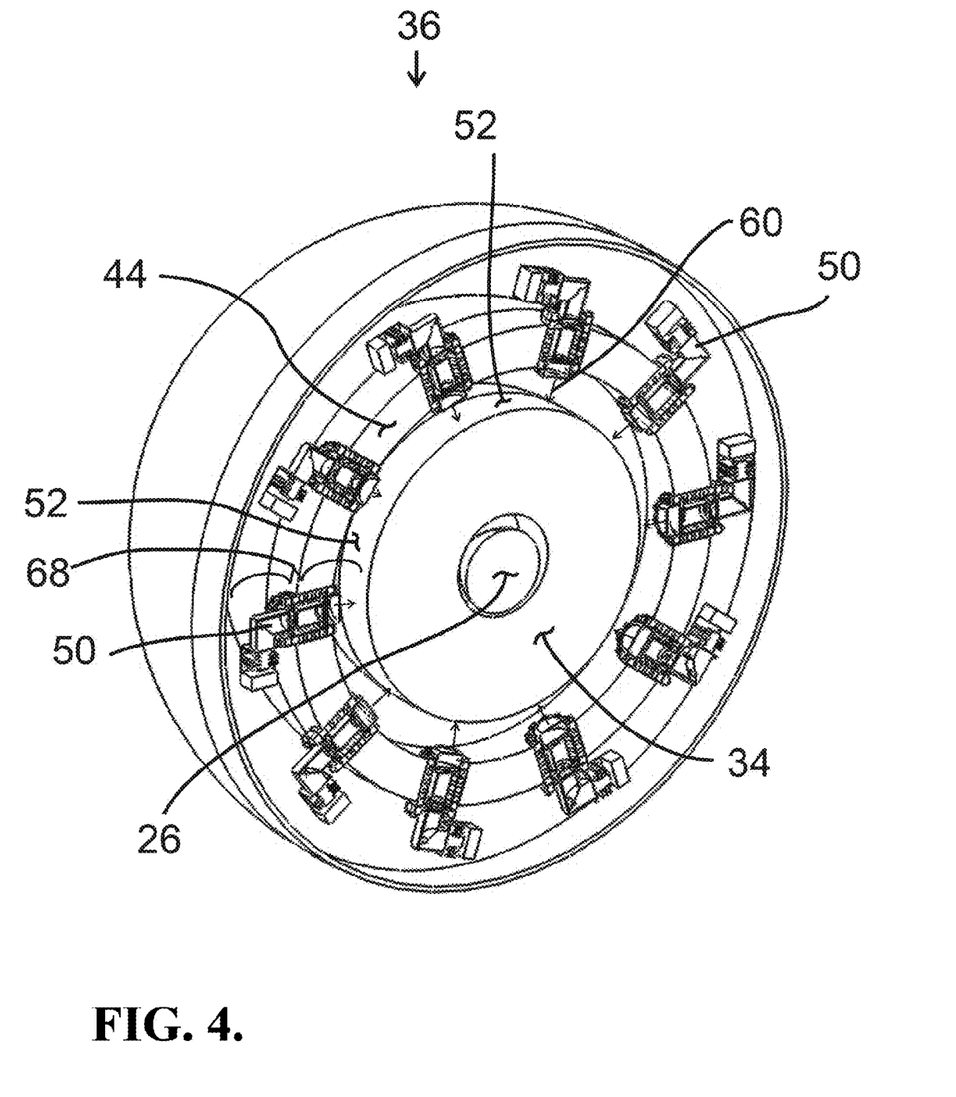
FIG. 4 is a cross sectional view of the arrangement of FIG. 3 with the patient's head inside the interior of the neutron irradiation system.

A cross section perspective view of the hemispheric neutron irradiation system 36 in an embodiment of the invention is shown in FIG. 4. This cross section view is of a radial cut directly through the patient's head 26 and hemispherical neutron irradiation system 36. As shown in this embodiment, ten fast-neutron generators 68 composed of ion sources 50 with titanium targets 52 are radially surrounding the hemispheric moderator 34 and the patient's head 26. The titanium target 52 in this embodiment is a continuous belt of titanium surrounding the moderator 34. The titanium targets can also be segmented, as was shown in FIG. 2. The ion sources in this embodiment are embedded in fast neutron reflector 44.

There are a number of materials one could select for the moderator 34 to achieve maximum thermal neutron flux at the patient's head 26. The performance of HDPE, heavy water ($D_2O$), graphite, $^7$LiF, and $AlF_3$ was analyzed using the Monte Carlo Neutral Particle (MCNP) simulation. In general, there is an optimum thickness for each moderator material that generates the maximum thermal flux at the patient's head (or other body part or organ). The thermal neutrons/($cm^2$-s) was calculated for these materials as a function of moderator thickness $d_3$, where $d_4$=25 cm, and fast neutron reflector 44 is $d_1$=50 cm thick and is made of lead. As in all our calculations, the combined fast neutron yield striking the area from all the fast neutron generators 68 is assumed in the MCNP to be $10^{11}$ n/s. The optimum thickness, range of thicknesses and maximum thermal neutron flux (E<0.5 eV) are given in Table I for various moderator materials. These are approximate values given to help determine the general dimensions of the moderator.

TABLE I

| | Moderator Thickness | | |
|---|---|---|---|
| Moderator Material | Optimum Thickness $d_3$ (cm) | Range of thickness $d_3$ (cm) | Maximum Flux (n/cm$^2$-sec) |
| HDPE | 6 | 4-10 | $7 \times 10^8$ |
| $D_2O$ | 15 | 9-25 | $2 \times 10^8$ |
| Graphite | 20 | 19-20 | $9 \times 10^7$ |
| $^7$LiF | 25 | 20-30 | $3 \times 10^7$ |
| $AlF_3$ | 30 | 20-40 | $1.5 \times 10^7$ |

The calculation of the therapeutic ratio is also important and depends upon the organ in question (brain, liver) and the body mass of the patient. Although HDPE gives the highest flux, it gives a lower therapeutic ratio compared to $^7$LiF. The designer is expected to do calculations similar to this to determine the optimum geometry for the neutron irradiation system.

The MCNP simulation was used to determine the delivered dose and therapeutic ratio to the patient 58 and compare it to a planar neutron irradiation system. In one simulation, moderator 34 is composed of Li F$_3$ whose thickness is $d_3$=25 cm. The inner diameter of the moderator (hole for head) is $d_4$=25 cm. The spacing between hemispheric fast neutron reflector 44 and hemispheric moderator 34 is $d_2$=10 cm. The head is assumed to be 28 cm by 34 cm. Fast neutron reflector 44 is made of $d_1$=20 cm thick lead in one embodiment. Thicker values of $d_1$ increase the tumor dose rate. At a thickness of 10 cm, the tumor dose rate is about one-half the value at a thickness of 50 cm. Fast neutron generators 68 are assumed to emit a total yield of $10^{11}$ n/sec. The combined titanium targets 52 give a total neutron emission area of 1401 cm$^2$.

In the MCNP simulation BPA (Boronophenylalanine) was used as a delivery drug. The concentration of boron in the tumor was 68.3 µg/gm and in the healthy tissue was 19 µg/gm. The calculated neutron dose rates in Gy-equivalent/hr are plotted in FIG. 5 as a function of distance from the skin to the center of the head. The calculated dose rates are comparable to those used for gamma radiotherapy, typically 1.8 to 2.0 Gy per session. For the same dosage, at a rate of 3 Gy-equivalent/hr, the session length would be from 30 to 40 min. long. These session times are considered reasonable for a patient to undergo.

Figure 6:
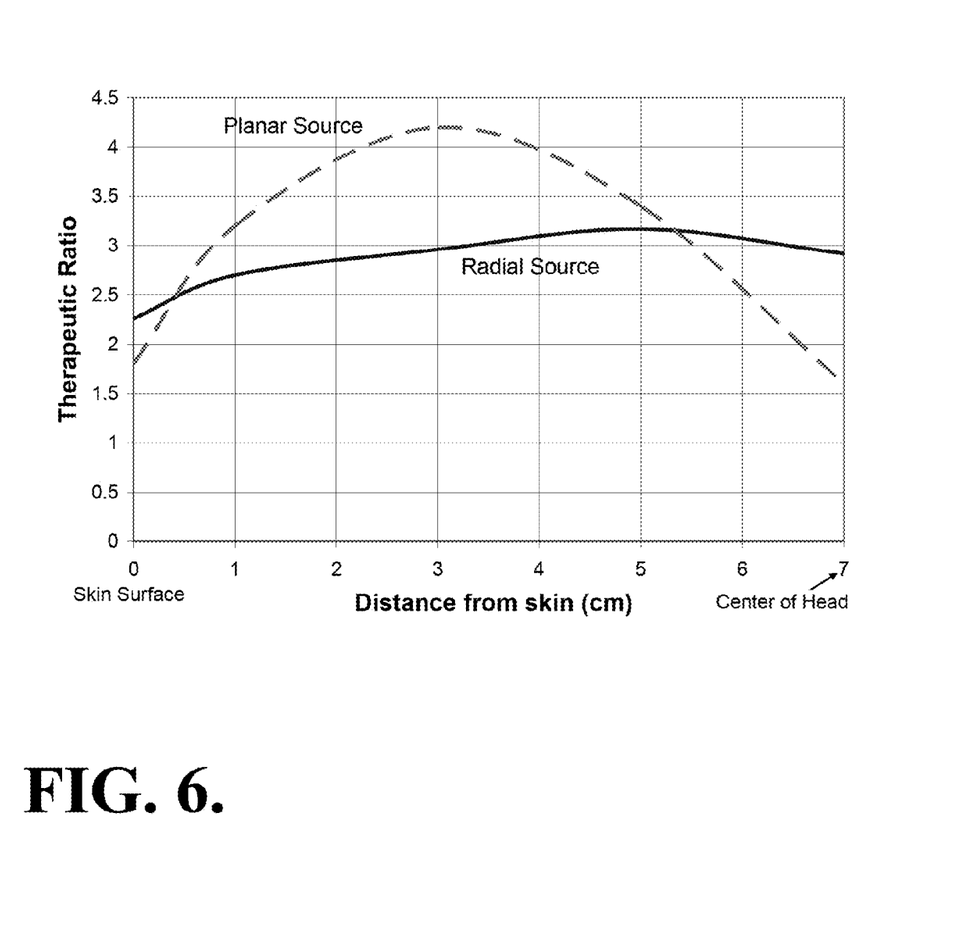
FIG. 6 is a graph of the therapeutic ratio as a function of distance from the surface of the head (skin) for the hemispheric (radial source) and planar moderator geometries in an embodiment of the invention.

For this simulation, the therapeutic ratio for the hemispherical neutron irradiation system is plotted in FIG. 6 as a function of distance from the skin to the center of the skull. The therapeutic ratio is defined as the delivered tumor dose divided by the maximum dose to healthy tissue. A therapeutic ratio of greater than 3 is considered adequate for cancer therapy.

Figure 5:
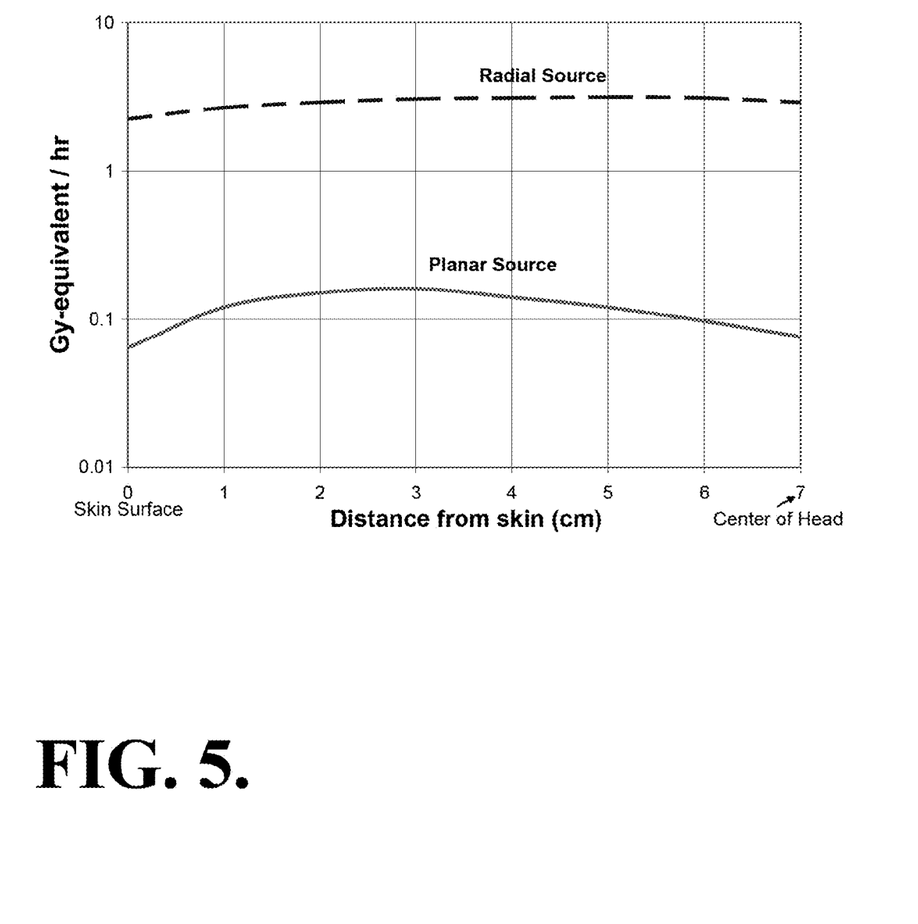
FIG. 5 is a graph of the dose rate (Gy-equivalent/hr) as a function of distance from the surface of the head (skin) for the planar and hemispheric moderator (radial source) geometries.

The conventional planar neutron irradiation system requires larger fast-neutron yields ($10^{12}$ to $10^{13}$ n/s) to achieve equivalent does rates and therapeutic ratios. In FIG. 5, a planar neutron irradiation system 14 of FIG. 1 is compared with that of a hemispheric neutron irradiation system 36 (FIGS. 2, 3, 4) in one embodiment of the present invention, using the same source of fast neutrons ($10^{11}$ n/s). As can be seen from FIG. 5, the hemispherical neutron irradiation system (called radial source in FIG. 5) achieves a dose rate of about a factor of 20 over that of the conventional planar neutron irradiation system 14. The planar geometry needs a fast neutron source of 2×$10^{12}$ n/s to achieve the same results. Indeed, if a DD fusion generator is used, then the planar source requires a factor of 20× increase in wall-plug power or 2.0 MW, a prohibitively large power requirement.

In addition, as can be seen from FIG. 5, over a ±5 cm distance across the head center, hemispheric neutron irradiation system 36 has less than a 10% variation in dosage. A uniform dose rate is crucial for the treatment of GBM, where we want to maintain a maximum therapeutic ratio and tumors may have distributed themselves across the brain.

Hemispherical neutron radiation system 36 in embodiments of the invention also gives a more uniform therapeutic ratio (FIG. 6) across the brain. The ratio is more uniform for the radial source and requires only $\frac{1}{20}^{th}$ of the fast neutron yield of the planar source (FIG. 1).

Other materials can be used for hemispheric moderator 34 in alternative embodiments. As those skilled in the art will know, high density polyethylene (HDPE), heavy water (D$_2$O), Graphite and $^7$LiF can also be used. In addition, combinations of materials (e.g. 40% Al and 60% AlF$_3$) can also be used. Different thicknesses $d_1$ of moderator can be used to optimize the neutron flux and give the highest therapeutic ratio.

The term "neutron generator or source" is intended to cover a wide range of devices for the generation of neutrons. The least expensive and most compact generator is the "fusion neutron generator" that produces neutrons by fusing isotopes of hydrogen (e.g. tritium and deuterium) by accelerating them together using modest acceleration energies. These fusion neutron generators are compact and relatively inexpensive compared to linear accelerators that can produce directed neutron beams.

Other embodiments depend upon the selection of the plasma ion source that is used to generate the neutrons at the cylindrical target. These are (1) the RF-driven plasma ion source using a loop RF antenna, (2) the microwave-driven electron cyclotron resonance (ECR) plasma ion source, (3) the RF-driven spiral antenna plasma ion source, (4) the multicusp plasma ion source and (5) the Penning diode plasma ion source. All plasma ion sources can be used to create deuterium or tritium ions for fast neutron generation. Cylindrical Irradiation System for the Liver and Other Cancer Sites.

Figure 7A:
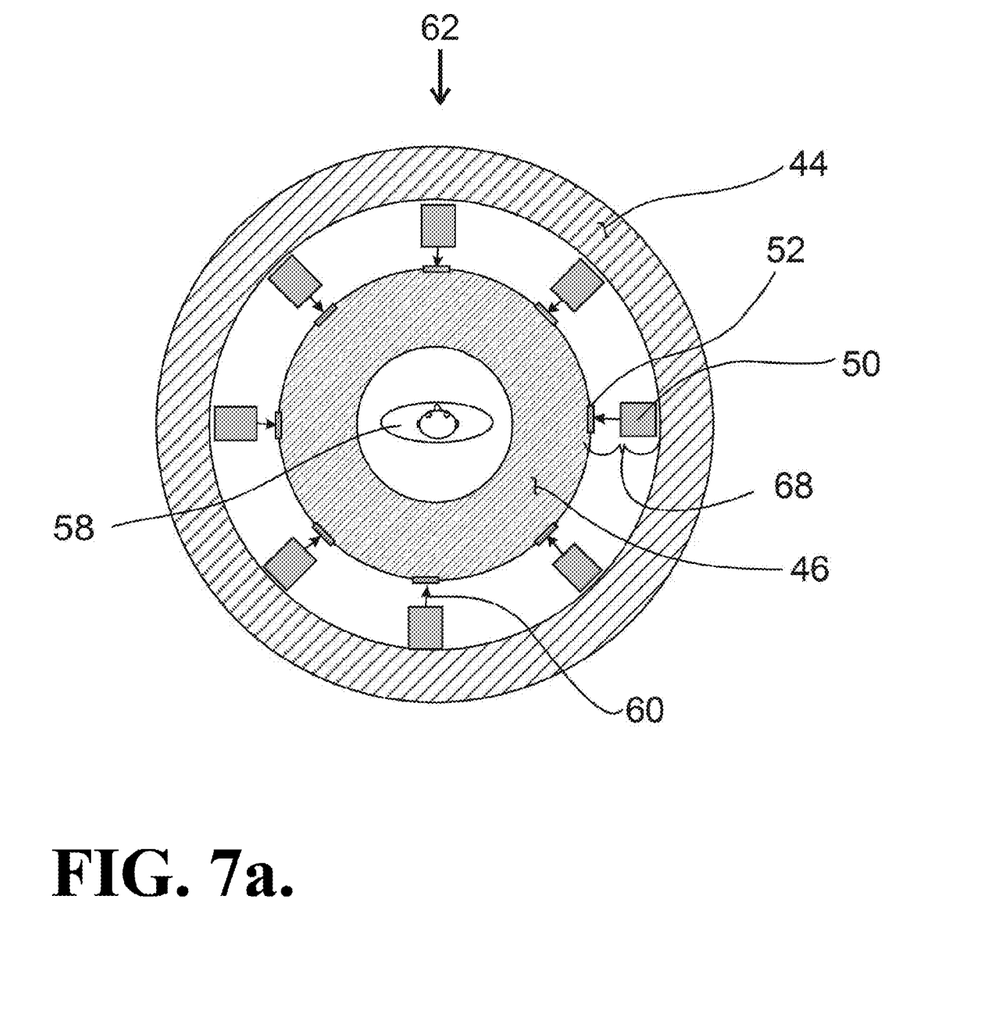
FIG. 7a is a cross sectional view of an embodiment of a cylindrical neutron irradiation system for the liver and other organs of the body.
Figure 7B:
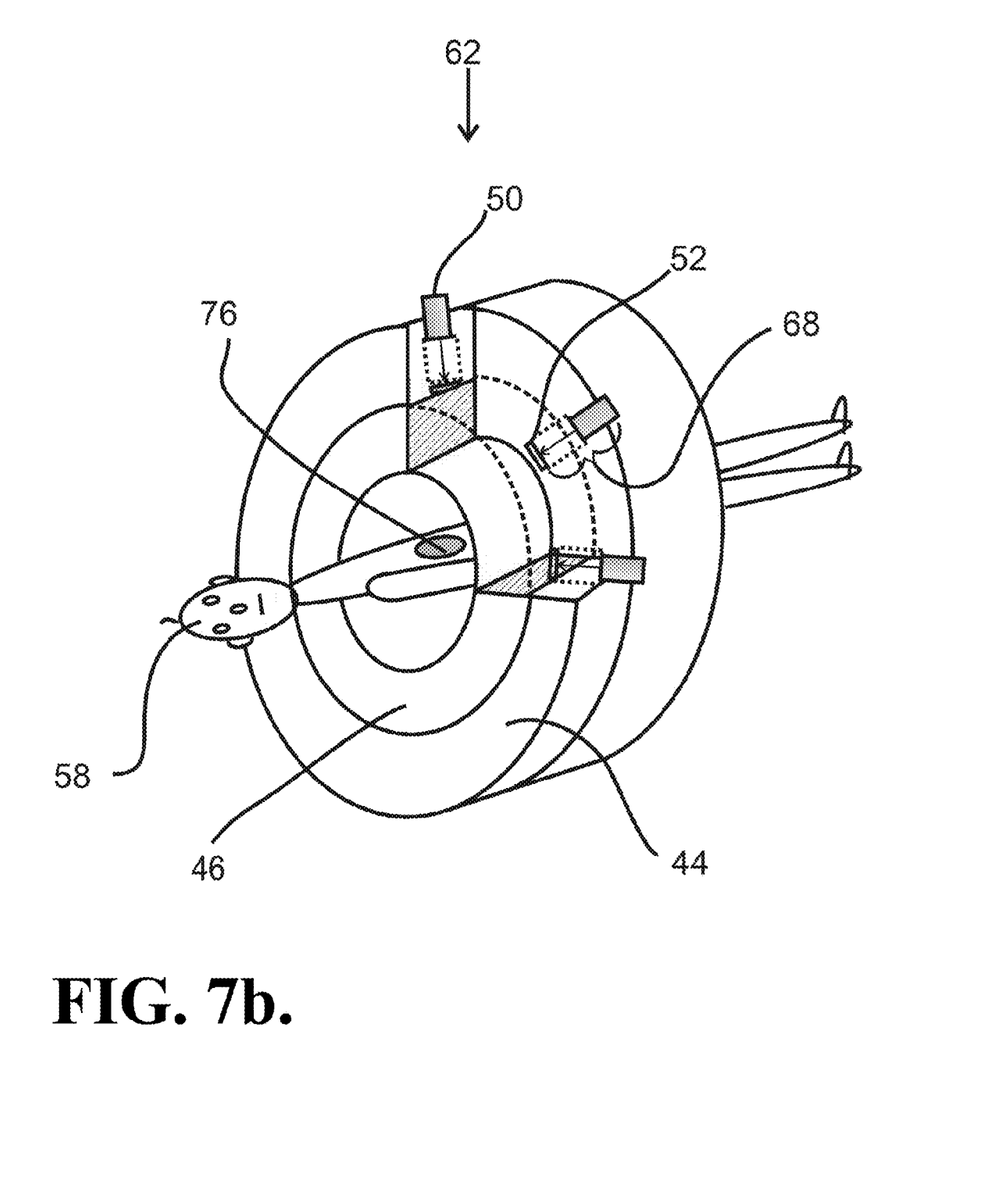
FIG. 7b is a perspective view of the cylindrical neutron irradiation system for the liver and other organs of a body.

FIG. 7*a* and *b* shows another embodiment of the invention which uses a cylindrical geometry to irradiate other organs and parts of patient 58, such as the liver 76. FIG. 7*a* is a cross sectional view of cylindrical neutron irradiation system 62 and FIG. 7*b* is a perspective view of the same embodiment. In this embodiment eight fast-neutron generators 68 surround a cylindrical moderator 46. These generators 68 all emit their fast neutrons at the surface of the moderator. A cylindrical fast neutron reflector 44 surrounds the cylindrical moderator 46.

As in the case of the hemispheric moderator 34, the cylindrical moderator 62 can be composed of well known moderating materials such as $^7$LiF, high density polyethylene (HDPE), and heavy water. These are shaped in a cylinder that surrounds the patient. The optimum thickness of the cylinder moderator for neutron capture purposes is dependent upon the material nuclear structure and density.

In this embodiment fusion neutron generators are used to supply the fast neutrons. Fast neutron generator 68 is composed of a titanium target 52 and an ion source 50 as before. The titanium targets are contiguous to the cylindrical moderator 46. Ion beams 60 are accelerated using a DC high voltage (e.g. 100 kV) to the titanium target 52 where fast neutrons are produced from the DD fusion reaction. The fast neutrons are emitted isotropically from the titanium targets 52 on the moderator, some moving out to the fast neutron reflector 44 and others inwardly to be moderated immediately to epithermal or thermal energies. Those reflected come back in to the cylindrical moderator 46 where they are moderated to epithermal and thermal energies, making their way finally to the patient 58.

Cylindrical neutron irradiation system 62 permits uniform illumination of a section of the patient's body (e.g. liver) as compared to the conventional planar neutron irradiation system. s in the case of the brain, the body itself acts as part of the moderation process, thermalizing epithermal neutrons coming in from cylindrical moderator 46.

As one skilled in the art will realize, other cancers, such as throat and neck tumors, can be effectively irradiated by a hemispherical neutron irradiation system such as system 36. The thickness and material content of the moderator can be adjusted to maximize the desired energy of the neutrons that enter the patient. For example, for throat and neck tumors, the moderator can be made of deuterated polyethylene or heavy water ($D_2O$) to maximize thermal neutron irradiation of the tumor near the surface of the body. For deeper penetration of the neutrons one might make the moderator out of $AlF_3$, producing epithermal neutrons. These would be optimum for reaching the liver and producing uniform illumination of that organ.

Segmented Moderator

In yet another embodiment, fast neutron sources with segmented moderators may be individually moved so as to achieve a uniform dose across the liver or other cancer site. This geometry produces a uniform thermal neutron dose with a factor of between $1/10^{th}$ and $1/20^{th}$ of the required fast neutron yield and line-voltage input power of previous linear designs. This again permits the use of the relatively safe deuterium-deuterium (DD) fusion reaction (no radioactive tritium) and off-the-shelf high voltage power supplies operating at modest power ($\leq 100$ kW).

Figure 8:
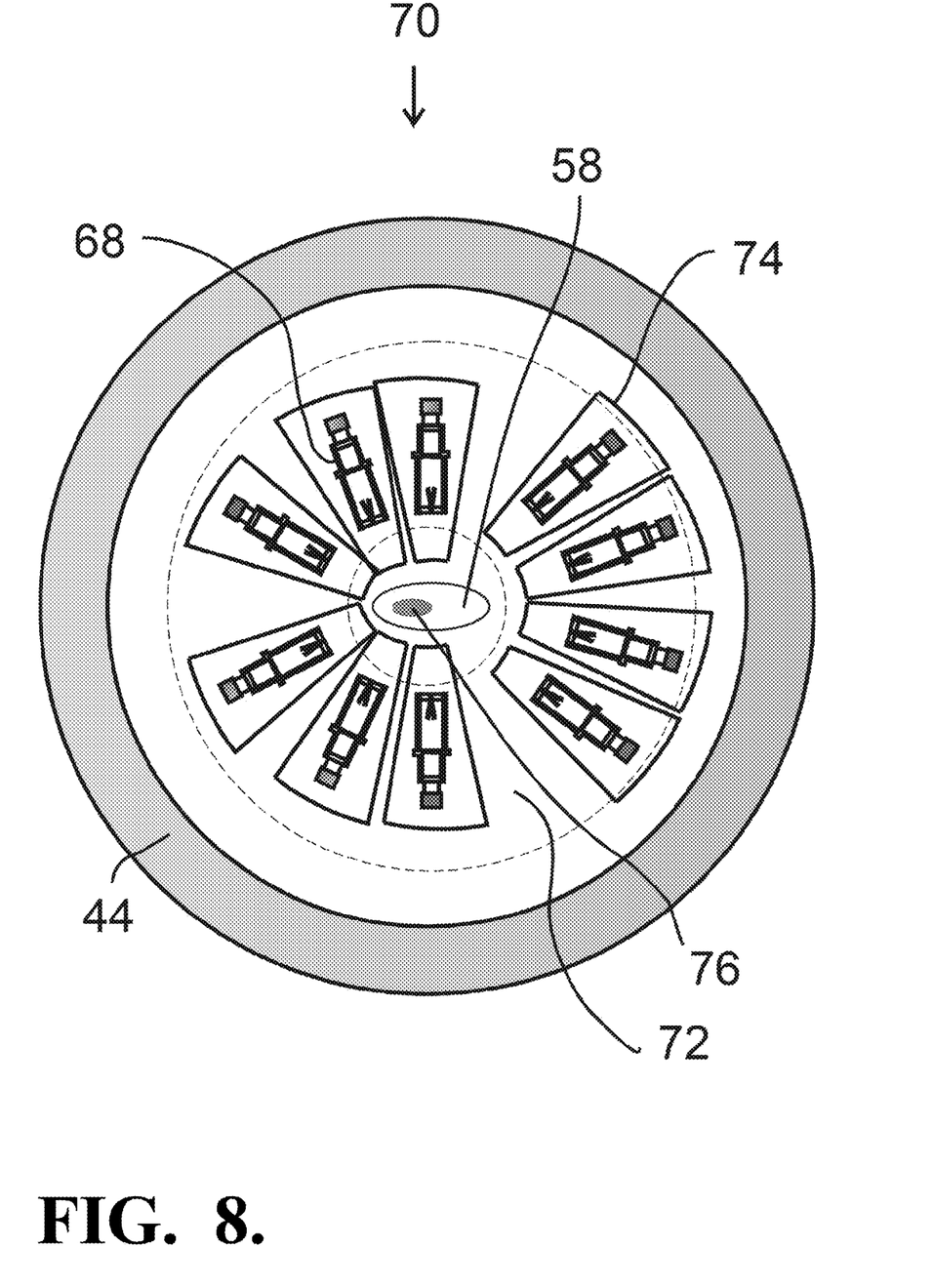
FIG. 8 is a cross sectional view of one of the embodiments of a neutron irradiation system wherein the neutron generators can be controlled independently to maximize thermal neutron flux at the liver or other organ of a body.

A segmented neutron irradiation system 70 in an embodiment of the invention is shown in FIG. 8. Ten fast neutron generators 68, each with a wedge-shaped moderator 74, surround the patient 58. The exact shape of each moderator can vary and can be of other geometries. Each generator and moderator pair can be moved independently of the others to achieve uniformity of the neutron flux across the liver, organ, or body part.

In between the wedge shaped moderators 74 more moderating material ("filler moderating material" 72) is inserted, forming a large single moderator. The "filler" moderating material 72 can be heavy water or powered moderating materials such as $AlF_3$. Pie shaped fillers of moderating material can also be fitted into the spaces between the wedge shaped moderator 74. Since neutrons scatter easily, there can be some space between the wedge shaped moderators 74 and the pie shaped fillers with out undue loss of neutron moderating efficiency.

The neutron yield from and the position of each fast neutron generator 68 can be adjusted to achieve uniformity across the liver or body part. The position and the neutron yield of the generator can be varied to achieve the desired radiation dose at a particular location in the patient's body. Since the cancer can be located in any part of the body, this benefit can be particularly useful for optimizing the dose at the cancer site.

Surrounding the entire fast neutron/moderator system is a cylindrical fast neutron reflector 44. Fast neutrons are produced by the fast neutron generators 68, and enter the moderators 74 where they are elastically scattered by collisions with the moderator atoms' nuclei, slowing them down after a few collisions to epithermal energies. As in the other embodiments, these epithermal neutrons enter the patient 58 and liver 76, wherein they are moderated further to thermal neutron energies.

The invention in various embodiments provides a uniform dose of thermal neutrons to the liver, organ or body part while minimizing fast neutron and gamma contributions. The required amount of fast neutrons (e.g. $2 \times 10^{11}$ n/s) to initiate this performance is again reduced compared to that (e.g. $2 \times 10^{13}$ n/s) needed for the planar neutron irradiation system of the prior art.

Figure 9:
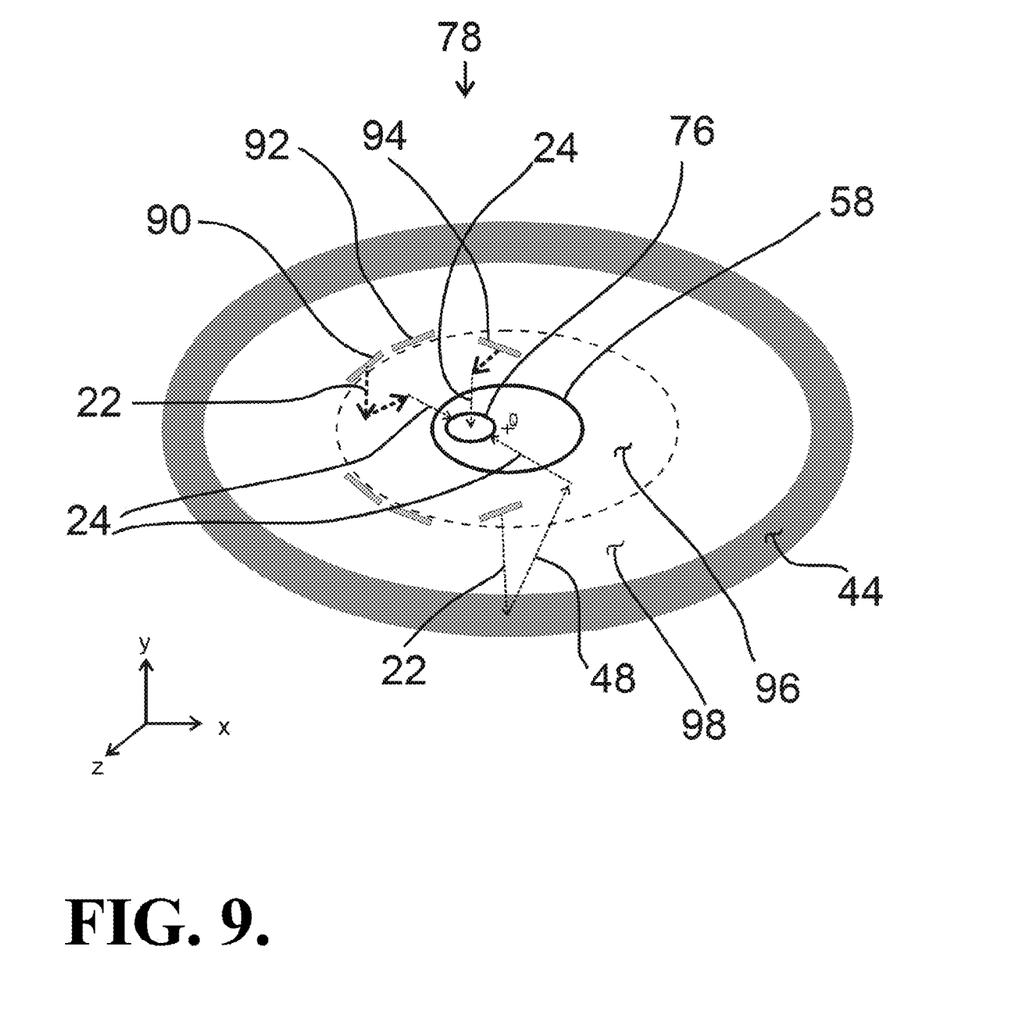
FIG. 9 is a simplified view of the cross section of the irradiation system that uses neutron generators that can be controlled independently of one another.

Another embodiment of the segmented design is shown in FIG. 9. The shape of the neutron irradiation system 78 is elliptical, with six sources of fast neutrons shown as distributed targets embedded in the inside elliptical moderator 96. Fast neutrons 22 are emitted isotropically in all directions. Those fast neutrons 22 moving outwardly are reflected back (see arrow 48) by fast neutron reflector 44, while fast neutrons traveling inwardly 22 are moderated to epithermal energies and enter the liver 76, where further moderation of the neutrons to thermal energies occurs. The inside elliptical moderator 96, outside elliptical moderator 98, reflector 44 and patient's body 58 act together to moderate and concentrate the thermal neutrons into the patient's liver 76. With a careful positioning of the moderators and fast neutron sources 90, 92, 94, a uniform dose can be achieved across the patient's liver, and, with a boron drug administered to the tumor, an excellent therapeutic ratio can be achieved.

Elliptical neutron irradiation system 78 in FIG. 9 is a simplified cross sectional view of the patient 58 inside the elliptical moderator 96. This cross section view is of a radial cut directly through the patient's torso and the moderator and fast neutron generator system. To maintain visual simplicity, only the titanium targets are shown and not the ion sources. Thus six fast-neutron sources are represented by three flat titanium targets 90, 92, 94. The rest of the fast neutron generator is not shown. Other components (e.g. plasma ion source) are neglected in the analysis. The wedge-shaped moderators 74 (used in FIG. 8) are also not shown in FIG. 9.

For a simple simulation of the neutron irradiation system, the targets 90, 92, 94 are the sources of the fast neutrons and are arranged in an elliptical material 96 (e.g. $AlF_3$, LiF). The effect of the moderating material 96, the fast neutron reflector 44 and the patient's body 58 were calculated using a Monte Carlo N-particle (MCN P5) transport code to determine how fast the neutrons were converted to thermal neutrons in the neutron irradiation system.

Dosage calculations were made along a central axis of the liver. The fast neutron sources (titanium targets) are 2 cm×2 cm in area, each producing $10^{11}/N$ n/s, where N is the number of sources. The human body 58 dimensions are 35.5 cm along the major axis and 22.9 cm along the minor axis. The inner elliptical moderator 96 is made of $^7LiF$ and 10 cm thick, while the outer moderator 98 is made of $AlF_3$ and 40 cm thick. The fast neutron reflector 44 is made of lead 50 cm thick. Boron-10 concentration is 19.0 μg/g in the healthy tissue and 68.3 μg/g in the tumor. The six sources are located in cms at: (−15,18.06,0) (−15,−18.06,0) (−17,17,0) (−17,−17,0) (0,15.85,0) (0,−15.85,0). These measurements are made along the axis of the liver 76 from the point (−15,0,0) to (−5,0,0). In the x-direction, the first two sources 90 are centered about the left edge of the liver shown in FIG. 9, the two sources 92 are centered about the edge of the body, and the third two 94 are located above and below the origin. The origin is shown in FIG. 9 as a small cross+ at the center of the body in the plane of the liver.

Figure 10:
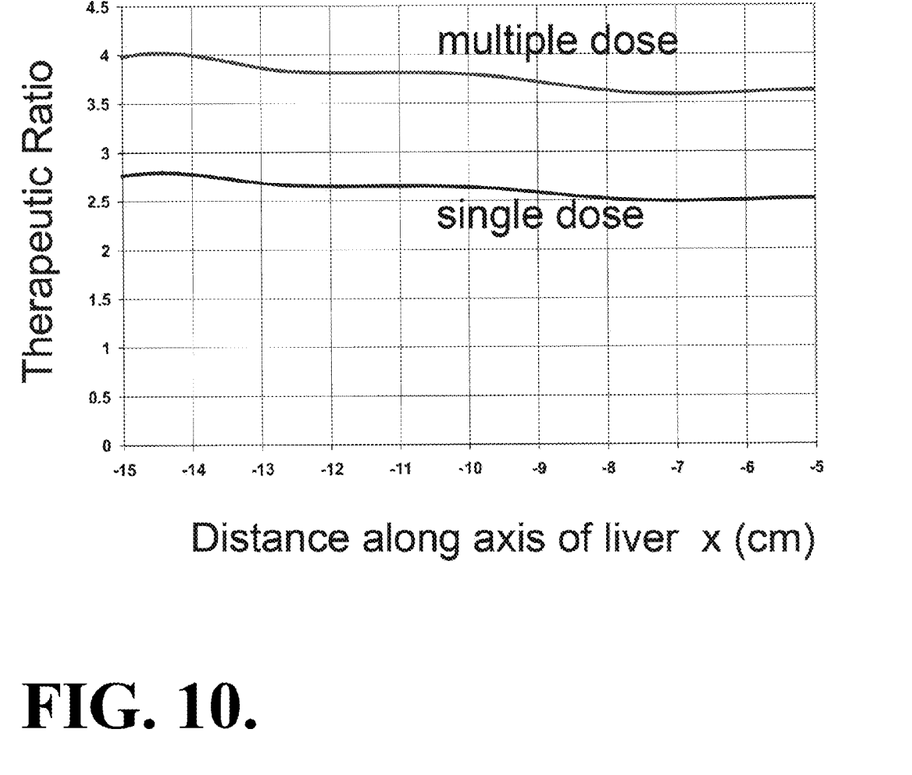
FIG. 10 is a graph of the therapeutic ratio as a function of distance along the axis of the liver in cm.

FIG. 10 shows the therapeutic ratio for a large single dose, and the therapeutic ratio for multiple small doses (where the photon dose to healthy tissue is not included) plotted as a function of distance along the axis of the liver. The photon dose can be neglected if there is some amount of time between doses. Many of the body's healthy cells can self repair and recover between doses. The expected therapeutic ratio is between these two curves when there is fractionation into multiple doses. In this simulation BPA was again used as the delivery drug with the concentration of boron in the tumor at 68.3 μg/gm and in the healthy tissue at 19 μg/gm.

Figure 11:
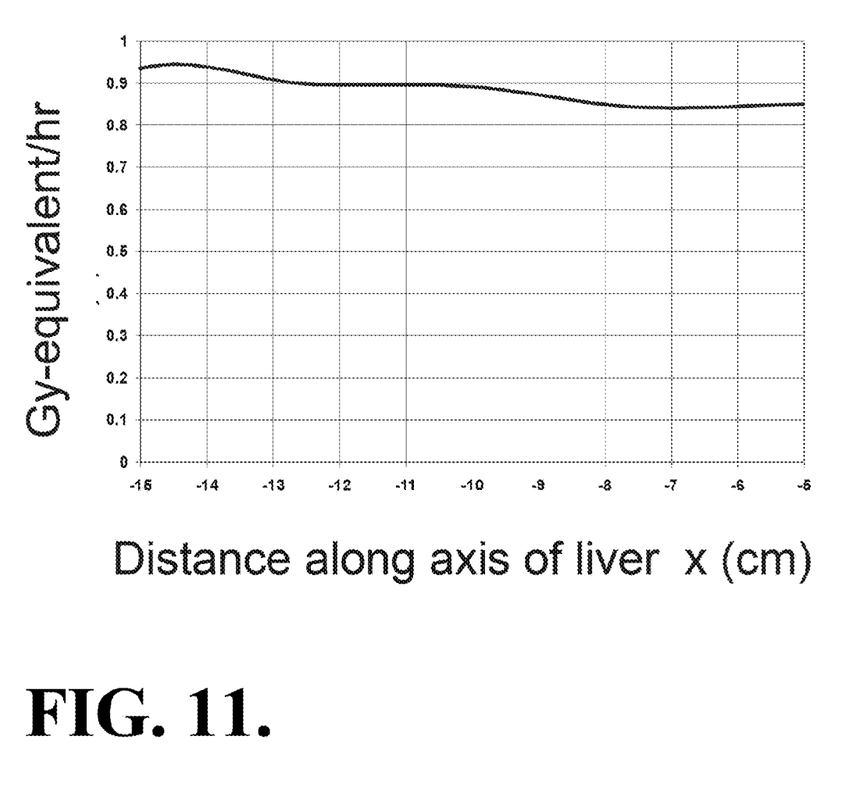
FIG. 11 is a graph of the dose rate as a function of distance along the axis of the liver in cm.

FIG. 11 indicates that the goal of having an extremely uniform dosage to the tumor has been achieved, with about ±6% variation along the x-dimension. The calculated dose rates are comparable to those used for gamma radiotherapy, typically 1.8 to 2.0 Gy-equivalent per hour if we increase the total neutron yield to $2\times10^{11}$ to $3\times10^{11}$ n/s. Thus at approximately $2\times10^{11}$ to $3\times10^{11}$ n/s it is possible to obtain a therapeutic ratio and uniform dosage to a tumor. Approximately 10 to 20 treatments of 30 to 40 minutes would be required, with a good therapeutic ratio, uniformity of dosage, and the opportunity for healthy tissue repair between treatments.

Once again the planar neutron irradiation systems require high fast neutron yields to drive them. In one prior art system known to the inventors a fast neutron source of $3\times10^{13}$ n/s is needed to obtain realistic treatment time of ~1-2 hours. Using a D-T neutron source with a yield $10^{14}$ n/s, acceptable treatment times were obtained (30 to 72 minutes with single beam and 63 to 128 minutes with 3 beams of different direction). But these are impossible yields to achieve with realistic wall plug powers. Instead of 50 to 100 kW for the hemispheric and cylindrical neutron irradiation systems, it would take a minimum of 0.5 MW to achieve adequate yield for the planar geometry with a DT generator. These are high powers for clinics and hospitals.

As one skilled in the art knows, other cancers, such as throat and neck tumors, can be effectively irradiated by the neutron irradiation system. The thickness and material content of the moderator can be adjusted to maximize the desired energy of the neutrons that enter the patient. For example, for throat and neck tumors, the moderator can be made of deuterated polyethylene or heavy water ($D_2O$) to maximize thermal neutron irradiation of the tumor near the surface of the body. For deeper penetration of the neutrons one might make the moderator out of $AlF_3$, producing epithermal neutrons. These would be optimum for reaching the liver and producing uniform illumination of that organ.

What is claimed is:

1. A neutron-capture therapy apparatus comprising:
    a cylindrical moderator structure composed primarily of a moderator material, having a length, an outside diameter, a cylindrical outer surface, an inside diameter, and a cylindrical inner surface, the inside diameter and length defining a treatment zone;
    a plurality of fusion neutron generators arranged in an array surrounding the cylindrical outer surface of the cylindrical moderator structure, each fusion neutron generator comprising an ion source emitting ions toward target material positioned at the cylindrical outside surface of the cylindrical moderator structure, the ions accelerated toward the target material by a DC voltage imposed between the target material and the ion source, impingement of the ions at the target material producing fast neutrons by a fusion reaction in the target material; and
    a cylindrical fast neutron reflector surrounding the cylindrical moderator structure and the fusion neutron generators;
    wherein fast neutrons are emitted isotropically from the target material at a plurality of different positions around the cylindrical outer surface of the moderator structure as a result of ion bombardment, neutrons emitted in a direction toward the cylindrical fast neutron reflector are reflected back into the cylindrical moderator structure, and moderated epithermal neutrons enter the treatment zone across the entire cylindrical inner surface of the moderator structure.

2. The neutron-capture therapy apparatus of claim 1 wherein the ion sources are equally spaced apart in a circular array.

3. The neutron-capture therapy apparatus of claim 1 wherein the target material is titanium, and is provided at the cylindrical outside surface of the moderator structure as a plurality of targets, one target corresponding to each fusion neutron generator.

4. The neutron-capture therapy apparatus of claim 1 wherein the ion sources are embedded in the cylindrical fast neutron reflector.

5. The neutron-capture therapy apparatus of claim 1 wherein fast-neutron generators are embedded in the cylindrical moderator structure.

6. The neutron-capture therapy apparatus of claim 1 wherein the target material is contiguous around the cylindrical outside surface of the cylindrical moderator structure.

7. The neutron-capture therapy apparatus of claim 1 wherein the cylindrical moderator structure comprises a plurality of wedge-shaped elements, equal in number to the plurality of fast-neutron generators, and each fast-neutron generator is embedded in one wedge shaped moderator element.

8. The neutron-capture therapy apparatus of claim 7 wherein the wedge-shaped elements are adjustable in position, changing flux density at different positions in the treatment zone.

* * * * *